United States Patent
Kochanek et al.

(10) Patent No.: US 7,247,479 B2
(45) Date of Patent: Jul. 24, 2007

(54) PIGMENT EPITHELIAL CELL OF THE EYE, ITS PRODUCTION AND USE IN THERAPY OF AN EYE OR CNS DISEASE

(76) Inventors: Stefan Kochanek, Werthmannstr. 24, 50935, Köln (DE); Ulrich Schraermeyer, Weinstockstr. 4, 41466, Neuss (DE); Gabriele Thumann, Herderstr. 60, 50931, Köln (DE)

( * ) Notice: Subject to any disclaimer, the term of this patent is extended or adjusted under 35 U.S.C. 154(b) by 0 days.

(21) Appl. No.: 10/079,609

(22) Filed: Feb. 21, 2002

(65) Prior Publication Data

US 2003/0087859 A1 May 8, 2003

Related U.S. Application Data

(60) Provisional application No. 60/270,746, filed on Feb. 22, 2001.

(30) Foreign Application Priority Data

Feb. 21, 2001 (DE) ................. 101 08 412

(51) Int. Cl.
*C12N 5/00* (2006.01)
*C12N 5/02* (2006.01)
*C12N 15/00* (2006.01)

(52) U.S. Cl. ..................... 435/373; 435/455

(58) Field of Classification Search ............ 424/93.21, 424/93.2; 435/455, 456, 325, 368, 373, 374, 435/320.1

See application file for complete search history.

(56) References Cited

U.S. PATENT DOCUMENTS 6,667,176 B1 * 12/2003 Funk et al. ................. 435/363
2003/0045498 A1 * 3/2003 Kovesdi et al. ............... 514/44

OTHER PUBLICATIONS

U.S. Appl. No. 60/228,337.*
Tezel et al., Exp. Eye Res. 66, 807-815, 1998.*
Williams et al., Nature. Dec. 15, 1988;336(6200):684-7.*
Morsy et al. PNAS, vol. 95, 7866-7871, 1998.*
Anglade et al., "Recombinant Adenovirus-Mediated Gene Transfer Into the Adult Rat Retina," *Current Eye Research* 17:316-321 (1998).
Kumar-Singh et al., "Encapsidated Adenovirus Minichromosomes Allow Delivery and Expression of a 14 kb Dystrophin cDNA to Muscle Cells," *Human Molecular Genetics* 5:913-921 (1996).
Li et al., "In Vivo Transfer of a Reporter Gene to the Retina Mediated by an Adenoviral Vector," *Investigative Ophthalmology & Visual Science* 35:2543-2549 (1994).
Rakoczy et al., "Recombinant Adenovirus-Mediated Gene Delivery Into the Rat retinal Pigment Epithelium in vivo," *Australian and New Zealand Journal of Ophthalmology* 26:S56-S58 (1998).
Baffi et al., "Evaluation of Second Generation Adenoviral Vectors for Gene Delivery into Retinal Pigment Epithelial Cells" *IOVS.*, 39(4):S719, Abstract 3302-B128,1998.
Reichel et al., "Gene Transfer in Ophthalmology," *Ophtalmologe*, 96(9):570-577, 1999, with English translation.

* cited by examiner

*Primary Examiner*—Brian Whiteman
(74) *Attorney, Agent, or Firm*—Clark & Elbing LLP (57) ABSTRACT

The present invention relates to a pigment epithelial cell of the eye containing vector DNA of an adenoviral vector with large DNA capacity, to the improved isolation and cultivation of these cells and to methods for production and the use in the therapy of an eye or nerve disease.

7 Claims, 2 Drawing Sheets

PIGMENT EPITHELIAL CELL OF THE EYE, ITS PRODUCTION AND USE IN THERAPY OF AN EYE OR CNS DISEASE

CROSS-REFERENCES TO RELATED APPLICATIONS

This application claims the benefit of U.S. application Ser. No. 60/270,746, filed Feb. 22, 2001, and foreign patent application DE 10108412.9-41, filed Feb. 21, 2001 in Germany.

BACKGROUND

The present invention relates to a pigment epithelial cell of the eye comprising vector DNA of an adenoviral vector with large DNA capacity, to the improved isolation and cultivation of these cells and to methods for the production and the use in therapy of an eye or nerve disease.

The five primary senses of touch, sight, hearing, taste and smell serve to pick up information from the surroundings. About 75% of our perceptions involve the sense of sight. This high percentage makes it clear that sight is of predominant importance in our daily life. Consequently, a weakening of our vision represents a great intrusion into everyday life.

Figure 1:
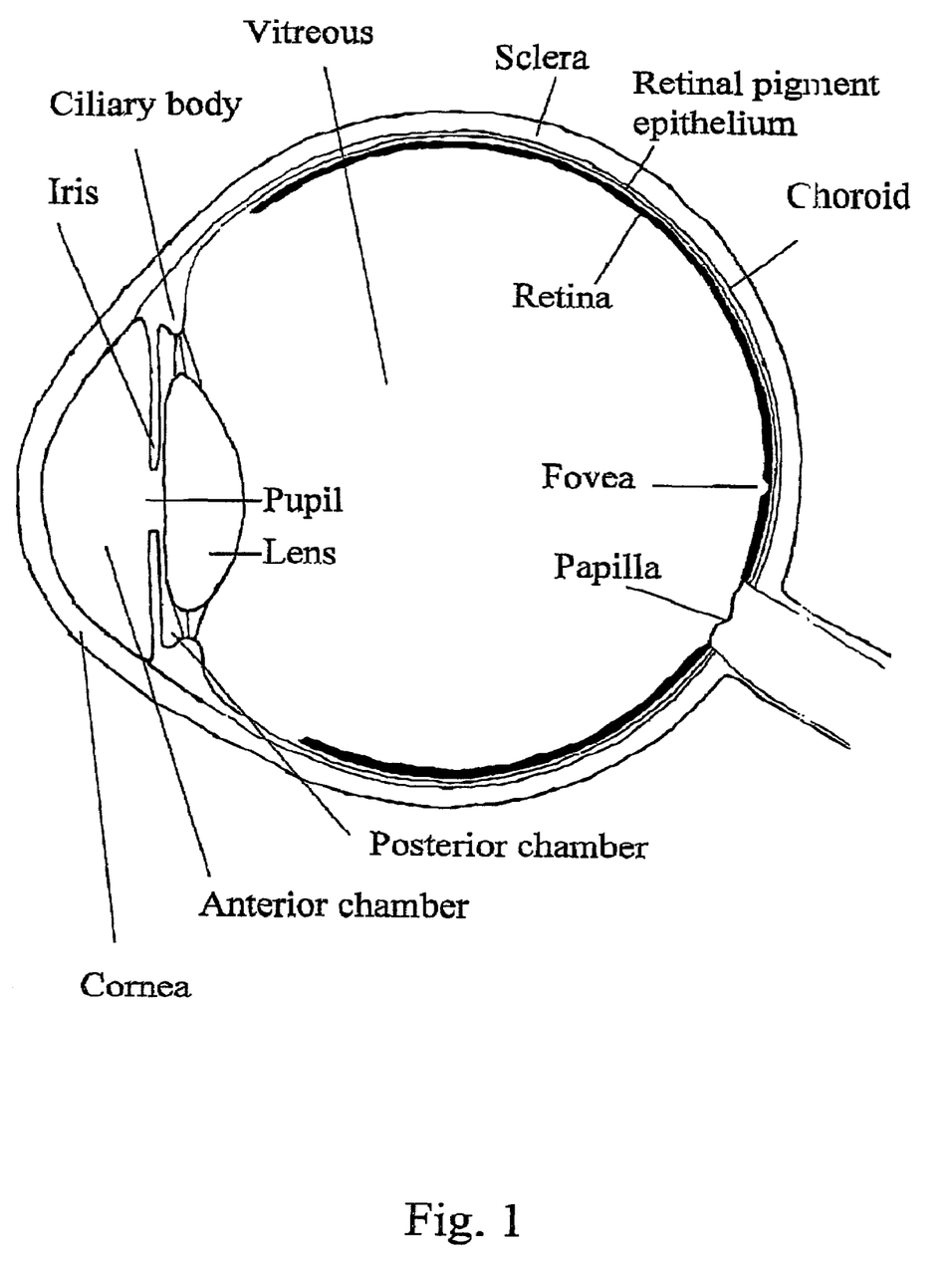
FIG. 1 Schematic cross section through the right eye.

The eye consists of a compound lens system which produces an image, which is inverted and reduced in size, of the surroundings on the retina. The dioptic apparatus consists of the transparent cornea, the iris forming the pupil, the lens and the vitreous body, a gelatinous, transparent mass inside the eyeball between lens and retina. FIG. 1 shows a schematic horizontal section through the eye. The covering of the eyeball consists of 3 layers: the sclera, the choroid and the retina. The retina in turn consists of an outer layer, the retinal pigment epithelium (RPE), and an inner layer, the neurosensory retina.

The annular iris separates the anterior from the posterior chamber of the eye and forms the anterior part of the uvea. From anterior to posterior it consists of a collagen-rich extracellular matrix, the iris stroma (it contains melanocytes, fibrocytes, nerves and blood vessels) and the iris pigment epithelium (IPE).

The iris pigment epithelium is in two layers and consists of an anterior and a posterior pigment epithelial cell layer (Freddo TF (1996) Ultrastructure of the iris. Microsc Res Tech 33: 369–389). The cells of the posterior iris pigment epithelium are connected by tight junctions. The anterior pigment epithelium has in addition smooth muscle cells (except in the region of the sphincter) which contribute to dilatation of the iris (Freddo 1996, supra). The iris pigment epithelium has the same embryological origin as the retinal pigment epithelium. It is possible to obtain about $2.3 \times 10^5$ IPE cells from a human iris, 90% of which survive in cell culture (Hu DN, Ritch R, McCormick SA, Pelton-Henrion K(1992) Isolation and cultivation of human iris pigment epithelium. Invest Ophthalmol Vis Sci 33: 2443–2453). IPE cells are highly pigmented and contain much eumelanin. Melanin has the following protective functions. It is able to bind divalent iron ions ($Fe^{2+}$) and other toxic substances (e.g. $Ca^{2+}$) and thus remove them from the cytoplasm of the cell (Hill HZ (1992) The function of melanin or six blind people examine an elephant. Bioessays 14: 49–56). Melanin is additionally able to convert $Fe^{2+}$ into less toxic $Fe^{3+}$ by redox reactions. On the other hand, the melanin synthesis precursors dihydroxyindole (DHI) and dihydroxyindolecarboxylic acid (DHIA) have a very strong antioxidant effect which is stronger than that of alpha-tocopherol (Memoli S, Napolitano A, d'Ischia M, Misuraca G, Palumbo A, Prota G (1997) Diffusible melanin-related metabolites are potent inhibitors of lipid peroxidation. Biochim Biophys Acta 1346: 61–68). Melanin is able to eliminate toxic oxygen free radicals produced in the eye by the high partial pressure of oxygen in combination with exposure to light. Elements important for the normal function of the retina, such as, for example, zinc, are moreover stored by melanin with great efficiency. Zinc, as a cofactor for, for example, antioxidative enzymes (superoxide dismutase) or connective tissue-degrading enzymes (metalloproteinases), has several important functions in the eye and in the central nervous system (CNS).

The pigment epithelium plays an import part in metabolism and in absorption of light in the eye. It is additionally responsible for the outer blood-retina barrier and for disposing of rejected photoreceptor cells. Consequently it forms an interesting target for the gene therapeutic treatment of eye diseases.

To date, a few experiments on the genetic modification of pigment epithelial cells have been described, but these provided unsatisfactory results in terms of the duration and stability of expression.

In a study with laboratory mice, a first generation adenoviral vector which expressed the *E.coli* lacZ gene under the control of the CMV promoter was used for gene transfer into the retinal pigment epithelium by subretinal injection. First generation adenoviral vectors (Gilardi et al., FEBS Letters 267, 60–62, 1990; Stratford-Perricaudet et al., Hum. Gene Ther. 1, 241–256, 1990) are characterized by deletions of the E1A and E1B genes. E1A and E1B have transforming and transactivating properties. In some vectors there is also deletion of E3 in order to increase the capacity to take up foreign DNA. Although the gene transfer into the retinal pigment epithelium was efficient and very good expression was observed shortly after injection in the retinal pigment epithelium, the expression was transient. 6 weeks after the injection, only a few lacZ-positive retinal pigment epithelial cells were still observable (Li T, Adamian M, Roof DJ, Berson EL, Dryia TP, Roessler BJ, Davidson BL (1994) In vivo transfer of a reporter gene to the retina mediated by an adenoviral vector. Invest Ophthalmol Vis Sci: 35, 2543–2549).

A further study carried out on laboratory rats with an observation period of 14 days used a first generation adenovirus which expressed the *E.coli* lacZ gene under the control of the Rous Sarcoma Virus (RSV) promoter. Although the gene transfer into the retinal pigment epithelium was efficient, and very good expression was observed 7 days after the injection in the retinal pigment epithelium, the expression was reduced one week later (Rakoczy PE, Lai CM, Shen WY, Daw N, Constable IJ (1998) Recombinant adenovirus-mediated gene delivery into the rat retinal pigment epithelium in vivo. Australian and New Zealand Journal of Ophthalmology 26 (Suppl.): S56–S58).

Another study carried out on 6-week-old RCS rats used a first generation adenoviral vector which expressed the green fluorescence protein (GFP) gene under the control of the CMV promoter (Anglade E, Csaky KG (1998) Recombinant adenovirus-mediated gene transfer into the adult rat retina. Curr Eye Res 17: 316–321). Although the gene transfer into the retinal pigment epithelium after subretinal injection was efficient, and 30 to 90% of the retinal pigment epithelium were GFP-positive in the region of the injection site 3 days after the injection, GFP expression was no longer detectable 6 days later (that is 9 days after the injection).

Whereas first generation adenoviral vectors were used in the above-mentioned examples of gene transfer in the region of the eye, in a further publication there was use of an adenoviral vector which is referred to as adenovirus minichromosome (EAM) for subretinal injection of mice (Kumar-Singh R, Farber DB (1998) Encapsidated adenovirus mini-chromosome-mediated delivery of genes to the retina: application to the rescue of photoreceptor degeneration. Hum Mol Genet 7: 1893–1900). This comprises a vector which does not express any viral proteins. The vector expressed the beta unit of cyclic GMP phosphodiesterase (PDE) under the control of the natural PDE promoter. The vector also expressed the E.coli lacZ gene under the control of the CMV promoter. In addition, the vector contained various E.coli plasmid elements (Plasmid backbone, ampicillin resistance gene, E.coli origin of replication). After production, the vector was characterized by pronounced variability of its genome. Monomeric and dimeric structures were observed, the latter in head-to-head, head-to-tail and tail-to-tail orientation. Because of this variability and the presence of plasmid sequences including antibiotic resistance, this vector is unsuitable for therapeutic use. The gene transfer experiments were carried out on rd mice which represent an animal model of retinal degeneration and are characterized by a mutation, which causes the degeneration, in the beta unit of the PDE gene. In this study, expression was detected exclusively in the neuronal portion of the retina but not in the retinal pigment epithelium. Although the neuronal cells are post-mitotic and thus no longer able to divide, expression of the PDE gene was only transient. Various methods (RT-PCR, Western blot analysis and determination of the PDE activity) were used to demonstrate that expression was no longer detectable 4 months after the injection.

To date, only the nonviral transfection reagent Lipofectamine has been used for transfecting IPE cells. In this study, the plasmid pXCN2-bFGF which expresses the rat bFGF cDNA was produced. The plasmid additionally contains a neomycin resistance gene. Cultivated rat IPE cells were transfected with this plasmid. The cells expressed the bFGF cDNA in vitro, and the authors write that degeneration of photoreceptors was delayed by up to 4 weeks in the RCS rat after subretinal transplantation as cell suspension (Tamai M, Yamada K, Takeda N, Tomita H, Abe T, Kojima S, Ishiguro I (1997) bFGF transfected iris pigment epithelial cells rescue photoreceptor cell degeneration in RCS rats. In: La Vail M, eds. Degenerative retinal diseases. 323–328). However, since, as shown in the work mentioned, the same effect, namely delayed degeneration of photoreceptors, was observed also in rats which had received IPE cells after transfection with a control plasmid by subretinal injection, and was not improved or extended by the transfection, this effect was not one which could be attributed to a targeted gene transfer but was explicable solely by the transplantation of the IPE cells. In addition, bFGF expression after transplantation was not demonstrated.

The publications mentioned therefore do not disclose an expression system for pigment epithelial cells of the eye with which long-term stable expression of an introduced gene can be observed. Long-term stable expression of such a gene is, however, necessary for the therapy of a large number of hereditary and acquired eye diseases. For many applications it is precisely the long-term production of therapeutic proteins which is the crucial factor for achieving a therapeutic effect.

SUMMARY

It is therefore an object of the present invention to provide pigment epithelial cells of the eye which can be employed in therapy.

The object is achieved by providing a pigment epithelial cell of the eye.

It has now been found, surprisingly, that a pigment epithelial cell of the eye which comprises vector DNA of an adenoviral vector with large DNA capacity shows long-term stable expression of at least one introduced gene and thus can be employed in therapy.

One aspect of the present invention is a pigment epithelial cell of the eye which comprises a vector DNA of an adenoviral vector with large DNA capacity.

A pigment epithelial cell of the eye means an epithelial cell of the eye in which pigment, for example melanin, is incorporated. An example of a pigment epithelial cell of the eye is a retinal pigment epithelial cell (RPE) or an iris pigment epithelial cell (IPE).

An adenoviral vector of large DNA capacity is understood by the skilled worker to be adenoviruses which comprise no viral coding DNA sequences (Kochanek S, Clemens PR, Mitani K, Chen HH, Chan S, Caskey CT (1996) A new adenoviral vector: Replacement of all viral coding sequences with 28 kb of DNA independently expressing both full-length dystrophin and beta-galactosidase. Proc Natl Acad Sci U.S.A. 93: 5731–5736; Fisher KJ, Choi H, Burda J, Chen SJ, Wilson JM. (1996); Recombinant adenovirus deleted of all viral genes for gene therapy of cystic fibrosis. Virology 217: 11–22; Kumar-Singh R, Chamberlain JS (1996) Encapsidated adenovirus minichromosomes allow delivery and expression of a 14 kb dystrophin cDNA to muscle cells. Hum Mol Genet 5: 913–921). These adenoviruses contain only the viral ends with inclusion of the inverted terminal repeats (ITRs) and the packaging signal. The capacity to take up foreign DNA is, for example, up to about 37 kb, because the predominant part of the adenoviral genome has been deleted.

Adenoviruses are particularly important as expression vectors, especially in the framework of gene therapy. One advantage of adenoviral vectors is the fact that these vectors are able to transduce replicating and nonreplicating cells efficiently in vitro and in vivo.

Various systems for producing adenoviral vectors of large DNA capacity have been described (Kochanek S (1999) High-capacity adenoviral vectors for gene transfer and somatic gene therapy. Hum Gene Ther 10: 2451–2459). The advantage of these adenoviral vectors with large DNA capacity compared with first and second generation adenoviral vectors is in particular the larger capacity. This makes it possible to introduce one or more genes or expression cassettes into the pigment epithelial cells.

After uptake of the adenoviral vector into the cell, the coat of the vector is normally broken down in endosomes. The remaining vector DNA is then transported into the cell nucleus and usually does not integrate into the cellular genome.

One example of an adenoviral vector with large DNA capacity is a vector which expresses the human alpha1-antitrypsin gene (Schiedner G, Morral N, Parks RJ, Wu Y, Koopmans SC, Langston C, Graham FL, Beaudet AL, Kochanek S (1998) Genomic DNA transfer with a high capacity adenovirus vector results in improved in vivo gene expression and decreased toxicity. Nature Genetics 18: 180–183). Another example is a vector which expresses the dystrophin gene and E.coli lacZ genes (Kochanek S, Clemens PR, Mitani K, Chen HH, Chan S, Caskey CT (1996) A new adenoviral vector: Replacement of all viral coding sequences with 28 kb of DNA independently expressing both full-length dystrophin and beta-galactosidase. Proc Natl Acad Sci U.S.A. 93: 5731–5736). In a preferred embodiment, HC-AdFK7 or HC-AdhCMV.PEDF is used as adenoviral vector with large DNA capacity. HC-AdFK7 is an adenoviral vector with large DNA capacity which expresses the enhanced green fluorescence protein (EGFP) under the control of the human cytomegalievirus promoter. HC-AdhCMV.PEDF is an adenoviral vector with large DNA capacity which expresses the human pigment epithelial cell-derived factor (PEDF) gene under the control of the cytomegalovirus promoter. In this vector, the PEDF protein is tagged by attachment (expression as fusion protein) of a polyhistidine epitope, so that the protein can easily be detected by use of an anti-polyhistidine antibody.

As shown in the examples, pigment epithelial cells can be transduced very efficiently in vitro with an adenoviral vector of large DNA capacity. As likewise shown in the examples, transplantation of these genetically modified cells is followed by a long-term gene expression which can be detected continuously for at least 4 months. It is evident that the transplantation site is not critical in this connection. After transplantation of the genetically modified pigment epithelial cells both into the eye in the subretinal space and, particularly surprisingly, into the CNS in the Corpus striatum led to long-term gene expression detectable for at least 4 months (eye) and at least 2 months (CNS).

Most experiments with these vectors have to date been carried out in the liver and in the skeletal muscle. Although liver gene transfer with a vector expressing human alpha1-antitrypsin into baboons (Morral N, O'Neal W, Rice K, Leland M, Kaplan J, Piedra P A, Zhou H, Parks RJ, Velji R, Aguilar-Cordova E, Wadsworth S, Graham FL, Kochanek S, Carey KD, Beaudet AL (1999) Administration of helper-dependent adenoviral vectors and sequential delivery of different vector serotype for long-term liver-directed gene transfer in baboons. Proc Natl Acad Sci USA 96: 12816–12821) was followed by longer-term expression (longer than one year) in two of three animals, in contrast to the present invention there was observed to be a continuous decrease in expression, which was still 19% of the initial levels in one of the animals after 16 months, and still 8% in the second animal after 24 months. In a third animal there was complete loss of expression within 10 weeks. There was speculation about the reason for the slow decrease in expression in the two animals with prolonged expression. Both growth of the animals and slow cell division of the hepatocytes were discussed. In the final analysis, the cause of the slow loss of expression is not explained. In the animal in which rapid loss of expression was observed, production of antibodies directed against human alpha 1-antitrypsin was observed.

A distinct decrease in expression of a LacZ reporter gene after gene transfer into the liver with an adenoviral vector of large DNA capacity within 30 days after the injection was observed in a further study (Parks RJ, Bramson JL, Wan Y, Addison CL, Graham FL (1999) Effects of stuffer DNA on transgene expression from helper-dependent adenovirus vectors. J Virol 73: 8027–8034).

Skeletal muscle is a tissue which, in terms of the natural turnover of the cells, resembles the pigment epithelial cells of the eye. Skeletal muscle cells are postmitotic cells. This means that they are similar to pigment epithelial cells in no longer dividing. There has been particular experience in gene transfer into the skeletal muscle of laboratory animals using adenoviral vectors of large DNA capacity. The gene transfer in these experiments was effected by direct injection into the tissue, similar to the present invention. Although expression over a prolonged period was observed after gene transfer using an adenoviral vectors of large DNA capacity which expressed both the dystrophin cDNA and the E.coli LacZ gene, it was observed that expression once again decreased within 84 days (Chen HH, Mack LM, Kelly R, Ontell M, Kochanek S, Clemens PR (1997) Persistence in muscle of an adenoviral vector that lacks all viral genes. Proc Natl Acad Sci USA 94: 1645–1650). There was complete loss of expression after 84 days in immunocompetent animals displaying no tolerance to E.coli beta-galactosidase.

In contrast to the experiments described in the literature, the stability of expression of genes introduced by gene transfer with an adenoviral vector of large DNA capacity into the pigment epithelial cell was surprisingly high. The advantages of adenoviral vectors of large DNA capacity in the transfection according to the invention of pigment epithelial cells of the eye compared with known transfection systems are accordingly the ensuring of stable gene expression;

the possibility of achieving regulated gene expression by use of constitutive, tissue-specific, regulatable promoters and regulatable expression systems;

the lack of immunogenicity and toxicity of the vector;

the high transduction efficiency on use of pigment epithelial cells.

In a preferred embodiment, therefore, the adenoviral vector comprises a therapeutic nucleic acid, in particular a therapeutic DNA, which does not originate from the adenoviral vector. This might be, for example, a therapeutic gene. A therapeutic gene is understood by the skilled worker to be a gene whose expression product can be used for the therapy or diagnosis of a disease.

A nucleic acid means a polymer which is cleaved on hydrolysis into sugars, in particular pentoses, especially ribose and deoxyribose, heterocyclic organic bases, in particular adenine, cytosine, guanine, thymine and uracil, and phosphoric acid. The nucleic acid may be, for example, a DNA or RNA. A therapeutic nucleic acid is a nucleic acid which itself or the product thereof has a therapeutic effect.

A gene means a linear DNA section which codes for a protein or an RNA. The therapeutic gene which is introduced by gene transfer into the pigment epithelial cell may vary in nature. The choice is determined by the therapeutic aim. For example, a gene which codes for a neurotrophic factors can be used. Examples of neurotrophic factors are the glial cell-derived neurotrophic factor (GDNF) and the pigment epithelial cell-derived factor (PEDF). It is also possible, for example, to use genes which prevent neoangiogenesis. One example is the soluble receptor for the vascular endothelial cell growth factor (VEGF) which is called soluble vascular endothelial cell growth factor receptor-1 (sflt1) (Roeckl W, Hecht D, Sztajer H, Waltenberger J, Yayon A, Weich HA (1998) Differential binding characteristics and cellular inhibition by soluble VEFG receptors 1 and 2. Experimental cell research 241:161–1709. Another example is a dominant-negative VEGF receptor 2 (KDR) (Machein MR, Risau W, Plate KH (1999) Antiangiogenic gene therapy in a rat glioma model using a dominant-negative vascular endothelial growth factor receptor 2. Hum Gene Ther 10: 1117–1128). Further therapeutic genes might be, for example, NGF, BDNF, CNTF, bFGF or neurotrophin 3,4–5.

PEDF has a very strong neurotrophic and neuroprotective effect (King G L, Suzuma K (2000) Pigment-epitheliumderived factor—a key coordinator of retinal neuronal and vascular functions. N Engl J Med 342: 349–351). This factor is produced by RPE under normoxic conditions. Production is stopped during hypoxia. This greatly promotes neovascularization. In age-related macular degeneration (AMD) the damaged RPE cells produce too little PEDF. This produces uncontrolled neoangiogenesis. The central effect of PEDF in the eye is to prevent neogenesis of vessels.

It is therefore possible according to the present invention for a genetically modified pigment epithelial cell to be a pigment epithelial cell which, after genetic modification with a PEDF-expressing adenoviral vector of large DNA capacity, secretes PEDF. This cell can then, for example, be transplanted into the subretinal space near the macula of patients following surgical removal of neovascularization membranes. The pigment epithelial cell is thus able on the one hand to replace the removed retinal pigment epithelium, and on the other hand to produce the PEDF factor essential for preventing neovascularization. Vision is stabilized in this way. PEDF is additionally able to protect from glutamate-mediated neurotoxicity.

It is additionally possible, depending on the cause of the disease, for various therapeutic genes to be expressed, singly or in combination, by the adenoviral vectors of large DNA capacity.

In another preferred embodiment, the gene is under the control of a viral or nonviral promoter which has constitutive, tissue-specific and/or regulatable activity.

A promoter which has constitutive activity means a promoter which mediates transcription of the downstream gene in virtually all tissues and virtually independently of the physiological state of the cell. An example of a promoter which has constitutive activity is the SV40 or the cytomegalovirus promoter.

A tissue-specific promoter means a promoter which mediates transcription of the downstream gene only in a particular tissue. Use of the tissue-specific promoter allows a protein or a functional RNA to be expressed tissue-specifically in IPE or in RPE cells. An example of such a tissue-specific promoter is the transthyretin promoter, which has good activity in RPE and in IPE cells.

A regulatable promoter means a promoter which mediates the transcription of a gene for example depending on the metabolic situation in the cell, the concentration of a molecule or the temperature. Gene expression can be controlled quantitatively and qualitatively by use of a regulatable promoter. An example of a regulatable promoter is a promoter which is activated in the event of hypoxia through inclusion of a hypoxia-sensitive element (Boast K, Binley K, Iqball S, Price T, Spearman H, Kingsman S, Kingsman A, Naylor S (1999) Characterization of physiologically regulated vectors for the treatment of ischemic disease. Hum Gene Ther 10: 2197–2208).

However, it is also possible to use a regulatable expression system which, for example, is induced or inactivated on administration of a medicament. An example of such a system is a tetracycline-dependent gene expression system (Freundlieb S, Schirra-Muller C, Bujard H (1999) A tetracycline controlled activation/repression system with increased potential for gene transfer into mammalian cells. J Gene Med 1:4–12).

After transduction of the pigment epithelial cell with an adenoviral vector with large DNA capacity, the cell is able to produce therapeutic proteins or RNAs. The therapeutic protein is a protein which causes a therapeutic effect. An analogous statement applies to a therapeutic RNA, for example an antisense RNA or a ribozyme. Examples of therapeutic proteins are the neurotrophic factors PEDF, GDNF, NGF, BDNF, CNTF, bFGF or neurotrophin 3,4–5 (Friedman WJ, Black IB, Kaplan DR (1998) Distribution of the neurotrophins brain-derived neurotrophic factor, neurotrophin-3, and neurotrophin-4/5 in the postnatal rat brain: an immunocytochemical study. Neuroscience 84: 101–114) and factors with antiangiogenetic activity, such as, for example, the soluble VEGF receptor-1 (sflt-1), the dominant-negative VEGFR-2 (KDR), and once again PEDF, which also has an antiangiogenetic activity in addition to its neurotrophic function (Dawson DW, Volpert OV, Gillis P, Crawford SE, Xu H, Benedict W, Bouck NP (1999) Pigment epithelium-derived factor: a potent inhibitor of angiogenesis. Science 285: 245–248).

Further examples of therapeutic genes are lysosomal enzymes (Cingle KA, Kalski RS, Bruner WE, O'Brien CM, Erhard P, Wyszynski RE (1996) Age-related changes of glycosidases in human retinal pigment epithelium. Curr Eye Res 115: 433–438) alpha-mannosidase, beta-galactosidase, N-acetyl-beta-glucosaminidase and N-acetyl-beta-galactosaminidase, and lipase. These enzymes play an important part in the breakdown of visual cell membranes and may be reduced in AMD.

Some more examples are genes which code for antioxidative enzymes (superoxide dismutase, catalase, peroxidases) because they may likewise be involved in the pathogenesis of AMD (Frank R N, Amin R H, Puklin J E (1999) Antioxidant enzymes in the macular retinal pigment epithelium of eyes with neovascular age-related macular degeneration, J Ophthalmol 127: 694–709).

Further examples are genes for gene products which are able to increase choroidal blood flow, for example NO synthases, because reduced choroidal blood flow may be involved in the pathogenesis of AMD (Luksch A, Polak K, Beier C, Polska E, Wolzt M, Domer G T, Eichler H G, Schmetterer L (2000) Effects of systemic NO synthase inhibition on choroidal and optic nerve head blood flow in healthy subjects. Invest Ophthalmol Vis Sci 41: 3080–3084).

A further aspect of the present invention is a pigment epithelial cell in a fixed assemblage of cells, called a cell sheet. To date, only single cell suspensions of autologous IPE cells have always been transplanted during experimental therapy of AMD. The advantage of such cell sheets is that the cells can be sited distinctly better by the transplantation technique, and that migration of cells away from the site of transplantation is prevented. Pigment epithelial cells in a fixed assemblage of cells are characterized by the assemblage of cells consisting of at least about 100, preferably about 1000, particularly preferably about 10000, pigment epithelial cells, and the latter not being separable from one another by moderate shear forces, in particular by repeated, for example ten-fold, movement up and down in a solution using a pipette.

A further aspect of the present invention is a cultivation system comprising at least one pigment epithelial cell of the eye and a feeder layer. The growing of IPE and RPE cells after isolation thereof is usually very time-consuming. The cultivation system of the invention allows large numbers of IPE and RPE cells to be produced in a very short time.

A feeder layer is understood by the skilled worker to mean cells which are cocultivated with other cells (target cells) and have a beneficial effect on the growth of the target cells. A beneficial effect may mean, for example, a faster growth of the cells or prevention of differentiation or dedifferentiation. This takes place, for example, by the cells of the feeder layer secreting molecules into the medium which then have a beneficial effect on growth of the target cells.

Inactivated fibroblasts are normally used as feeder layer for cultivating embryonic stem cells. Inactivation of the fibroblasts can be achieved, for example, by treatment with mitomycin C or by exposure to y rays. It is possible, for example, to use fibroblasts from a mammal, in particular mouse or human. In one implement, the fibroblasts and pigment epithelial cells of the same species, in particular of the same individual, are used. However, the fibroblasts may also be a permanent cell line, for example STO fibroblasts or 3T3 fibroblasts, or primary embryonic fibroblasts. The production of fibroblasts is known to the skilled worker (e.g. Abbondanzo S, Gadi I, Stewart C (1993) Derivation of embryonic stem cell lines. Methods in Enzymology 225: 803–823).

The cultivation system might, for example, comprise a culture vessel in which the pigment epithelial cells of the eye and the feeder layer are cultivated directly adjacent to one another, in particular one on top of the other, in a suitable medium. The different cells [lacuna], however, also be cultivated in a culture vessel spatially separate from one another so that the exchange of, for example, factors to stimulate growth takes place solely through the medium.

A further aspect of the present invention is a method for the production of a pigment epithelial cell of the eye, where the cell is genetically modified with the aid of an adenoviral vector of large DNA capacity.

A genetic modification is understood by the skilled worker to be any alteration of the genetic information of the cells. This can be achieved, for example, by addition, insertion, substitution and/or deletion of one or more nucleotides. In a particular embodiment, the genetic modification is brought about by gene transfer, it being possible for the gene to be, for example, present extrachromosomally in the cell.

Gene transfer means the introduction of one or more genes into, for example, a cell. In the present invention it is possible, for example, for at least one gene to be introduced with the aid of an adenoviral vector with large DNA capacity into a pigment epithelial cell. cDNAs are normally used. However, it is also possible to use the genes themselves (including their introns and exons). In another embodiment, however, it is also possible to introduce a genetically modified, naturally occurring gene or synthetic nucleic acids into the pigment epithelial cell.

A further aspect of the present invention is a method for the production of a pigment epithelial cell of the eye comprising an adenoviral vector of large DNA capacity, where the cell is cultivated in serum-free medium, in the presence of a feeder layer and/or in a fixed assemblage of cells.

To isolate pigment epithelial cells in a fixed assemblage of cells, the iris or a part of the iris, or the retina, in particular in the peripheral retinal region, is separated, for example mechanically or enzymatically, in particular with Accutase, chondroitinase and/or heparinase, in particular from the stroma and the basal membrane. The cell sheet can then be cultivated further in cell culture. If required, the cell sheets can be broken down into single cells by renewed incubation with Accutase.

It has been possible to show within the scope of the present invention that a cell culture medium which contains no serum, for example fetal calf serum, has a beneficial effect on the growth of pigment epithelial cells of the eye.

A further aspect of the present invention is the use of genetically modified pigment epithelial cells for the therapy of eye diseases, possibilities being both a hereditary and an acquired eye disease. Examples of acquired or hereditary eye diseases are age-related macular degeneration, glaucoma and diabetic retinopathy.

Age-related macular degeneration (AMD) is the commonest reason for legal blindness in western countries. Atrophy of the submacular retinal pigment epithelium and the development of choroidal neovascularizations (CNV) results secondarily in loss of central visual acuity. For the majority of patients with subfoveal CNV and geographic atrophy there is at present no treatment available to prevent loss of central visual acuity. Early signs of AMD are deposits (druses) between retinal pigment epithelium and Bruch's membrane. During the disease there is sprouting of choroid vessels into the subretinal space of the macula. This leads to loss of central vision and reading ability. An example of a therapeutic gene which can be employed for therapy of AMD is the PEDF gene.

Glaucoma is the name given to a group of diseases in which the pressure in the eye increases abnormally. This leads to restrictions of the visual field and to the general diminution in the ability to see. The commonest form is primary glaucoma; two forms of this are distinguished: chronic obtuse-angle glaucoma and acute angle closure. Secondary glaucoma may be caused by infections, tumors or injuries. A third type, hereditary glaucoma, is usually derived from developmental disturbances during pregnancy. The aqueous humor in the eyeball is under a certain pressure which is necessary for the optical properties of the eye. This intraocular pressure is normally 15 to 20 millimeters of mercury and is controlled by the equilibrium between aqueous production and aqueous outflow. In glaucoma, the outflow of the aqueous humor in the angle of the anterior chamber is blocked so that the pressure inside the eye rises. Glaucoma usually develops in middle or advanced age, but hereditary forms and diseases are not uncommon in children and adolescents. Although the intraocular pressure is only slightly raised and there are moreover no evident symptoms, gradual damage occurs, especially restriction of the visual field. Acute angle closure by contrast causes pain, redness, dilation of the pupils and severe disturbances of vision. The cornea becomes cloudy, and the intraocular pressure is greatly increased. As the disease progresses, the visual field becomes increasingly narrower, which can easily be detected using a perimeter, an ophthalmological instrument. Chronic glaucoma generally responds well to locally administered medicaments which enhance aqueous outflow. Systemic active substances are sometimes given to reduce aqueous production. However, medicinal treatment is not always successful. If medicinal therapy fails, laser therapy or conventional operations are used in order to create a new outflow for the aqueous humor. Acute glaucoma is a medical emergency. If the intraocular pressure is not reduced within 24 hours, permanent damage occurs.

A numbers of growth or neurotrophic factors are able to withstand the survival of glaucomatous neurons. These include NGF, BDNF, CNTF, bFGF and neurotrophin 3,4–5. It would be possible in a preferred embodiment to use genetically modified pigment epithelial cells which contain as therapeutic gene the gene for NGF, BDNF, CNTF, bFGF and/or neurotrophin 3,4–5 for the therapy of glaucoma. These factors would then be able to regulate the survival by activating specific metabolic pathways. Many of these factors have a short half-life. Stable expression of these factors is accordingly of considerable therapeutic importance.

Diabetic retinopathy arises in cases of diabetes mellitus [lacuna] thickening of the basal membrane of the vascular endothelial cells as a result of glycosilation of proteins. It is the cause of early vascular sclerosis and the formation of capillary aneurysms. These vascular changes lead over the course of years to diabetic retinopathy. The vascular changes cause hypoperfusion of capillary regions. This leads to lipoid deposits (hard exudates) and to vasoproliferation. The clinical course is variable in patients with diabetes mellitus. In age-related diabetes (type II diabetes), capillary aneurysms appear first. Thereafter, because of the impaired capillary perfusion, hard and soft exudates and dot-like hemorrhages in the retinal parenchyma appear. In later stages of diabetic retinopathy, the fatty deposits are arranged like a corona around the macula (retinitis circinata). These changes are frequently accompanied by edema at the posterior pole of the eye. If the edema involves the macula there is an acute serious deterioration in vision. The main problem in type I diabetes is the vascular proliferation in the region of the fundus of the eye. The standard therapy is laser coagulation of the affected regions of the fundus of the eye. The laser coagulation is initially performed focally in the affected areas of the retina. If the exudates persist, the area of laser coagulation is extended. The center of the retina with the site of sharpest vision, that is to say the macula and the papillomacular bundle, cannot be coagulated because the procedure would result in destruction of the parts of the retina which are most important for vision. If proliferation has already occurred, it is often necessary for the foci to be very densely pressed on the basis of the proliferation. This entails destruction of areas of the retina. The result is a corresponding loss of visual field. In type I diabetes, laser coagulation in good time is often the only chance of saving patients from blindness.

One example of a genetically related disease of the pigment epithelium is autosomal recessive severe retinal dystrophy which starts in childhood and is caused by mutation in the RPE65 gene (Gu S M, Thompson DA, Srikumari CR, Lorenz B, Finckh U, Nicoletti A, Murthy KR, Rathmann M, Kumaramanickavel G, Denton MJ, Gal A (1997) Mutations in RPE65 cause autosomal recessive childhood-onset severe retinal dystrophy. Nat Genet 17: 194–197. Correction of the pathological phenotype is to be expected from introduction of the RPE65 gene with the aid of an adenoviral vector with large DNA capacity.

It was additionally completely surprising that pigment epithelial cells of the eye can also be transplanted into the CNS. It was possible to show within the framework of the present invention that pigment epithelial cells survived the observation period of 5 weeks. Histological examination revealed no evidence of induction of damage to neural cells. Instead it was possible to observe that the pigment epithelial cells formed intensive contacts with neurons.

To date, a number of different cell types have been employed in animal experiments or in patients with Parkinson's disease in clinical studies:

Examples are fetal cells obtained from brains of human fetuses. Fetal cells from the ventral midbrain or dopaminergic neurons have already been transplanted in clinical studies on more than 300 patients with Parkinson's disease (for review, see Alexi T, Borlongan CV, Faull RL, Williams CE, Clark RG, Gluckman PD, Hughes PE (2000) (Neuroprotective strategies for basal ganglia degeneration: Parkinson's and Huntington's diseases. Prog Neurobiol 60: 409–470). A number of different cell types, including non-neuronal cells, e.g. cells from the adrenal cortex, Sertoli cells on the gonads or glomus cells from the carotid bodies, fibroblasts or astrocytes, have been used in patients with Parkinson's disease or in animal models with the aim of replacing dopamine spontaneously or after gene transfer (Alexi et al. 2000, supra). The survival rate of transplanted fetal dopaminergic neurons is 5–8%, which was enough to cause a slight improvement in the signs and symptoms (Alexi et al. 2000, supra).

In recent years, neuronal stem cells from brains of adult vertebrates have been isolated, expanded in vitro and reimplanted into the CNS, after which they differentiated into pure neurons. Their function in the CNS remains uncertain, however. Neuronal precursor cells have also been used for gene transfer (Raymon HK, Thode S, Zhou J, Friedman GC, Pardinas JR, Barrere C, Johnson RM, Sah DW (1999) Immortalized human dorsal root ganglion cells differentiate into neurons with nociceptive properties. J Neurosci 19: 5420–5428). Schwann cells which overexpressed NGF and GDNF had neuroprotective effects in models of Parkinsonism (Wilby MJ, Sinclair SR, Muir EM, Zietlow R, Adcock KH, Horellou P, Rogers JH, Dunnett SB, Fawcett JW (1999) A glial cell line-derived neurotrophic factor-secreting clone of the Schwann cell line SCTM41 enhances survival and fiber outgrowth from embryonic nigral neurons grafted to the striatum and to the lesioned substantia nigra. J Neurosci 19: 2301–2312).

The advantage of pigment epithelial cells, compared with cells used to date, especially on use of endogenous (autologous) cells, is that they are not rejected by the immune system and thus, as expected, have a very high survival rate. In addition, they replace natural melanin pigment which is lost in the substantia nigra of Parkinsonian patients. This melanin is able to detoxify free $Fe^{++}$ and thus has a beneficial effect on the progress of the disease.

Another aspect of the present invention is therefore the use of pigment epithelial cells for the therapy of nerve diseases, in particular a disease of the nervous system, preferably of the CNS, especially of Parkinson's disease.

An example of a common disease of the CNS is Parkinson's disease which is a chronic degenerative disease of the brain. The disease is caused by degeneration of specialized neuronal cells in the region of the basal ganglia. The death of dopaminergic neurons results in reduced synthesis of dopamine, an important neurotransmitter, in patients with Parkinson's disease. The standard therapy is medical therapy with L-dopa. L-Dopa is metabolized in the basal ganglia to dopamine and there takes over the function of the missing endogenous neurotransmitter. However, L-dopa therapy loses its activity after some years.

Pigment epithelial cells spontaneously produce some factors which have a neuroprotective effect. Examples of such factors are, which are produced, for example, by IPE cells, are nerve growth factor (NGF), ciliary neurotrophic factor (CNTF), basic fibroblast growth factor (bFGF) or factors with an angiogenic activity such as, for example, vascular endothelial growth factor (VEGF) or platelet-derived growth factors A and B (PDGF A+B). An example of a neurotrophic factor which can be produced in the genetically modified IPE cells after gene transfer is glial cell-derived neurotrophic factor (GDNF).

It is additionally possible to utilize the natural protective function of pigment epithelial cells. In Parkinson's disease, transplanted IPE cells may display a neuroprotective effect due to the antioxidant effect of their melanin granules. This could be caused by the ability of melanin and its precursors to bind $Fe^{2+}$ and other toxic substances (e.g. $Ca^{2+}$) and thus remove them from the cell cytoplasm (Hill HZ (1992) The function of melanin or six blind people examine an elephant. Bioessays 14: 49–56) or to have a very strong antioxidant effect. IPE cells have a high melanin content and also continue to form melanin when they are located in the retina, the subretinal space or the CNS. Unambiguous proof thereof is the presence of numerous early stages of melanogenesis (premelanosomes), detectable by electron microscopic studies. Melanin has antioxidant properties, protects from lipid peroxidation, is able directly to bind oxygen free radicals (Hill HZ (1992) The function of melanin or six blind people examine an elephant. Bioessays 14: 49–56) and can prevent the formation of new oxygen free radicals by binding metal cations (Memoli S, Napolitano A, d'Ischia M, Misuraca G, Palumbo A, Prota G (1997) Diffusible melanin-related metabolites are potent inhibitors of lipid peroxidation. Biochim Biophys Acta 1346: 61–68). If highly pigmented iris pigment epithelial cells are introduced into tissue with high oxidative stress, for example in the substantia nigra of patients with Parkinson's disease, or into the papilla of glaucoma patients, or into the vicinity of the macula of AMD patients, then a neuroprotective effect occurs simply through the presence of the melanin in the IPE cells.

An example of a protein with a good therapeutic potential for the therapy of patients with Parkinson's disease is glial cell-derived neurotrophic factor (GDNF), a survival factor for dopaminergic neurons. GDNF has effects even in picomolar concentrations on the survival rate and growth of dopaminergic neurons from embryonic brain. Animal experimental studies have shown that direct gene transfer into the substantia nigra of a GDNF expression cassette using various vectors (first generation adenoviral vectors, AAV vectors or lentiviral vectors) was able to protect dopaminergic neurons in the 6-OHDA rat model (Mandel RJ, Spratt SK, Snyder RO, Leff SE (1997) Midbrain injection of recombinant adeno-associated virus encoding rat glial cell line-derived neurotrophic factor protects nigral neurons in a progressive 6-hydroxydopamine-induced degeneration model of Parkinson's disease in rats. Proc Natl Acad Sci U.S.A. 94: 14083–14088). In a preferred embodiment, GDNF is expressed in autologous IPE cells after transduction with an adenoviral vector of large DNA capacity. The cells genetically modified in this way are then implanted stereotactically at the site of action, for example into the striatum. In a further embodiment, the gene coding for the therapeutic protein undergoes regulated expression, for example through use of a cell-specific promoter. In a preferred embodiment, the therapeutic gene is expressed regulatably, for example by use of a system which can be regulated by tetracycline.

In a preferred embodiment of this invention, pigment epithelial cells are implanted at the desired site in the CNS. The cells can be put at the desired site of action for example by injection, for example during a stereotactic operation. This makes it possible to produce specific therapeutic molecules in situ.

In a particularly preferred embodiment there is the use of autologous pigment epithelial cells. The use of autologous pigment epithelial cells has the following advantages compared with other cell types: no rejection reactions occur because the pigment epithelial cells used are derived from the patients themselves; in terms of developmental history, these are neuroepithelial cells histogenetically related to brain cells.

In a preferred embodiment of this invention, pigment epithelial cells, in particular autologous IPE cells, which are genetically modified are used for the therapy of CNS diseases, such as, for example, Parkinson's disease.

The pigment epithelial cells of the invention can additionally be used in transplantation. In one embodiment of the invention, the pigment epithelial-cells of the invention can display their therapeutic effect through transplantation into the eye.

The pigment epithelial cells can be transplanted, for example, into the choroid and exert there a therapeutic effect through production of pigment epithelial-endogenous factors or through production of therapeutic molecules after genetic modification with an adenoviral vector of large DNA capacity.

However, the pigment epithelial cells can also be employed in the region of the papilla. It has been possible to show within the scope of the present invention that, after injection into the posterior part of the vitreous, the cells migrate into the optic disk and there integrate into the tissue assemblage. This opens up the possibility of therapy of diseases manifested, for example, in the optic disk.

The pigment epithelial cells can also be injected into the vitreous, in particular through a transscleral access into the posterior part of the vitreous. It was possible to show, by fundoscopic inspection of RCS rats, that the IPE cells are found entirely on the papilla throughout an observation period of 2 months. It was histologically evident that the IPE cells had migrated into the optic disk and there formed intensive contact with the blood vessels and axons. Electronic microscopy shows no damage to neuronal cells or proliferation of IPE cells in the vitreous. This embodiment of the invention makes it possible, for example, to have direct access to the optic disk and to release or activate, with or without genetic modification, neuroprotective mediators in or in the direct vicinity of the papilla.

A further embodiment of the present invention relates to the use of adenoviral vectors with large DNA capacity for the genetic modification of pigment epithelial cells in vivo. As shown in the examples, in vivo transduction of RPE cells leads, through subretinal injection with an adenoviral vector of large DNA capacity, to a surprisingly stable expression for at least 6 months.

A further aspect of the present invention relates to a medicament or diagnostic aid comprising a pigment epithelial cell of the invention and suitable excipients and/or additives. Suitable excipients and additives, which serve, for example, to stabilize or preserve the medicament or diagnostic aid, are generally known to the skilled worker (see, for example, Sucker H et al. (1991) Pharmazeutische Technologie, $2^{nd}$ edition, Georg Thieme Verlag, Stuttgart). Examples of such excipients and/or additives are physiological saline solutions, Ringer dextrose, dextrose, Ringer lactate, demineralized water, stabilizers, antioxidants, complexing agents, antimicrobial compounds, proteinase inhibitors and/or inert gases.

The following figure and the examples are intended to explain the invention further without restricting it thereto.

DESCRIPTION OF THE FIGURE

The iris pigment epithelium is located on the side of the iris facing the lens. The macula is the region (about 6 mm in diameter) directly surrounding the fovea.

Features from left to right: left terminus of adenovirus type 5 (nt 1–440) including the packaging signal ψ; 20 kb of stuffer DNA fragment derived from the human HPRT locus (gene map positions 1777–21729, locus: HUMHPRTB); hCMV promoter and PEDF cDNA with a C-terminal 6His tag; SV40 poly A; 6.5 kb human fragment of C346 (cosmid map positions 10205–16750, locus: HUMDXS455A); right terminus of adenovirus type 5 (nt 35818–35935).

DETAILED DESCRIPTION OF THE INVENTION

1. Isolation of Cell Sheets

To isolate IPE cells in assemblages of cells (cell sheets), iridectomies were collected fresh from the operating theater after a trabeculectomy or a basal iridectomy, brought in F12 medium ((HAM) with L-glutamine, Gibco, Life Technologies, Paisely, Scotland) and directly processed further. Basal iridectomies of glaucoma patients or pieces of iris from rats or pigs were treated with Accutase (Cat. No. L11-007, PAALaboratories) in Dulbecco's PBS with 0.5 mmol/l EDTA×Na for 15–20 min. The tissue which can be obtained by an iridectomy has an area of about 3.5 mm$^2$ and contains about 20000 IPE cells. The cell layers were pipetted up and down very carefully with F12 medium and pipetted out on polystyrene. It was possible to detach the IPE cells completely as double cell layer with intact basal membrane from the stroma under the stereomicroscope as was demonstrable by examination under the electron microscope. It was possible to remove this basal membrane completely by incubation with 0.1 U/ml chondroitinase ABC (Sigma) and 2.4 U/ml heparinase (Sigma) in PBS at pH 7.4 and at 37 degrees Celsius for 2 hours. It was then possible to break the cell sheets down into single cells by renewed Accutase incubation for 5 minutes.

To isolate RPE cells in assemblages of cells (cell sheets), autologous RPE cell sheets and single cells were mechanically detached in the periphery of human eyes after local retinotomy, and aspirated with a canula. It was possible to remove 50,000 peripheral RPE cells locally without the patients later complaining of unpleasant serious losses of visual field. The removal of 50,000 RPE cells in each case was possible at several peripheral sites on the eye.

2. Growing of IPE and RPE Cells by Cultivation on Fibroblasts

IPE or RPE cells obtained from iridectomies or eyes of organ donors were cultivated on fibroblasts (mouse 3T3 fibroblast cell line), which served as feeder layer, in F12 medium. The cells become adherent to the fibroblasts within one day and start to proliferate. The number of cells tripled or quadrupled on the fibroblasts within 3 days. The fibroblasts had previously been treated with 40 μg/ml mitomycin C so that they die after no more than 10 days. A pure culture of pigment epithelial cells is obtained after this time.

3. Injection of IPE Cells

IPE cells were isolated as single cell suspension as described under 1. An animal model of age-dependent macula degeneration and of retinal degeneration caused by a specific phagocytosis defect and degeneration of the RPE is the Royal College of Surgeons Rat (RCS rat). Under Ketanest/Nembutal anesthesia, the upper conjunctiva of dystrophic RCS rats (18 days old) was opened by an incision 4 mm long and 4 mm posterior of the limbus. Kolibri forceps were used to hold the conjunctiva near the limbus firmly.

3.1. Subretinal Injection

In the subretinal injection, a 26 gage canula was used to pierce the sclera, choroid and retinal pigment epithelium at the level of the equator as far as the vitreous. A Hamilton syringe with a blunt 32 gage canula was introduced anteriorally 2–3 mm tangentially between retina and RPE. 60000 IPE cells were injected in 0.5 μl of cell culture medium (F 12 (HAM) with L-glutamine, Gibco, Life Technologies, Paisely Scotland). The RCS rats were sacrificed after completion of the observation period of 6 and 8 months. The eyes were enucleated. The corneas were removed and the remaining parts of the eyes were fixed in 3% glutaraldehyde. Areas with transplanted iris cells were easily identifiable from the pigmentation and were excised and embedded for electron microscopic investigations in accordance with a routine protocol. Under the electron microscope, surviving, i.e. morphologically intact, IPE cells were detectable in the subretinal space for up to 8 months after transplantation. Surviving photoreceptors with inner segments but without outer segments were present for up to 6 months after subretinal transplantation.

3.2. Injection into the Vitreous

Injection into the vitreous took place at the same site of the subretinal injection in 6 eyes. However, the canula was introduced like a secant of a circular arc 1–2 mm deep into the vitreous. 60000 IPE cells were injected close to the papilla. The vitreous and the lens remained clear in the observation period of 2 months. The IPE cells in all 6 eyes formed a macroscopically or funduscopically visible collection on the papilla. The histology showed that the IPE cells migrated into the optic disk. The cells were highly pigmented and there was no evidence of cell damage or proliferation.

3.3. Injection into the Choroid

The site chosen for injection into the choroid was the same as for subretinal injection. The sclera was cut with a pointed scalpel through an incision 1 mm long until the choroid was visible. The canula was placed perpendicular to the eyeball on the incision site and 60000 IPE cells in 0.5 μl of F12 medium were injected into the choroid. IPE cells transplanted into the choroid in 15 eyes, compared with 6 untreated eyes, led to a survival of photoreceptors for up to 6 months. Both the number of surviving photoreceptors/mm of retina ($p=0.020$) and the maximum nucleus height ($p=0.019$) were significantly different in the Mann-Whitney test from the untreated eyes (Table 1).

TABLE 1

Median, 25$^{th}$ and 75$^{th}$ percentiles of the number of photoreceptor cell nuclei still present, of the maximum thickness of the photoreceptor layer in semithin sections 6 months after transplantation of IPE cells into the choroid is indicated.

|  | Number of eyes | Photo-receptor nuclei [mm$^{-1}$] | Maximum height of the photoreceptor cell nuclei |
|---|---|---|---|
| IPE transplantation | 15 |  |  |
| Median |  | 12.3 | 1.0 |
| 25$^{th}$ Percentile |  | 0.0 | 0.0 |
| 75$^{th}$ Percentile |  | 45.5 | 3.0 |
| Control without treatment | 6 |  |  |
| Median |  |  |  |
| 25$^{th}$ Percentile |  | 0.0 | 0.0 |
| 75$^{th}$ Percentile |  | 0.0 | 0.0 |
|  |  | 0.0 | 0.0 |
| Mann-Whitney test P value |  | 0.020 | 0.019 |

4. Injection of Rat IPE Cells into the CNS

For the stereotactic implantation method, Wistar rats were anesthetized by intraperitoneal injection of 1 ml of avertin (2 g of tribromoethanol 3,3,3 (dry), 1 g of pentanol (liquid), 8 ml of 100% ethanol and 90 ml of 0.9% Nacl) per 100 g of body weight. The cranium was fixed in a precisely reproducible manner at three bone points, the external auditory canals and the maxilla so that the calvaria was horizontal at the level of the bregma. After the medial front-occipital skin incision, 1.5 cm long, the periostium was pushed aside in order to have a clear view of the cranium sutures which served as reference point for the stereotactic coordinates. The coordinates were determined on the basis of the atlas of Praxinos and Watson (Praxinos G. Watson C. The rat brain in stereotactic coordinates. 1986;2 end Dr., Academic Press, Sydney):

The puncture site was 1.5 mm in the frontal direction and 2 mm to the right parietally from the bregma. The upper portion of the striatum is at a depth of 4.5 mm. The hole with a diameter of about 0.5 mm was drilled at the appropriate position using a precision shaft drill (Proxxon, Minimot 401E) avoiding damage to the dura. 5–10 µl of the cell suspension were introduced through this drilled hole with a 25 µl N-702-N Hamilton syringe with fixed needle, injecting at a depth of 5 mm measured from the surface of the dura. 60000 IPE cells from Long Evans rats were injected into the striata of each of 4 Wistar rats. Before the needle was withdrawn, 2 min were allowed to elapse so that the cell suspension was able to diffuse into the tissue and the resulting local pressure could diminish. Otherwise there was a risk that cells could have followed the withdrawn needle into the puncture channel or into the overlying tissue sections. For the same reason, a further 30 sec were allowed to elapse after the needle had been withdrawn 4 mm, before it was completely removed. A skin suture was then applied.

After 5 weeks, the brains were perfusion-fixed with 3% glutaraldehyde in cacodylate buffer. Pigmented areas were excised from the striatum and embedded for electron microscopy.

The transplanted areas were easily identifiable macroscopically by the pigmentation. Under the electron microscope, the IPE cells had intact mitochondria and plasma membranes. They were highly pigmented, contained melanogenesis stages and formed contact zones with neurons. The IPE cells were always found singly without contacts with other IPE cells. They were also found 3–4 mm away from the puncture channel, which suggests active migration of the cells. The neurons adjacent to the IPE cells were morphologically intact. Immunocompetent cells (macrophages, lymphocytes) were not observed.

5. Genetic Modification

Isolated and adherent rat and human IPE cells were transduced in vitro with 20, 50 and 100 MOI (multiplicity of infection) of the adenoviral vector with large DNA capacity HC adenovirus "HC-AdFK7" which harbors the EGFP (enhanced green fluorescent protein) under the control of the human CMV (cytomegalovirus) promoter as transgene. For this purpose, 80% confluent cell cultures in F12 complete medium were incubated with the appropriately diluted virus stock solution at 37° C. for 24 hours. The medium was changed the next morning. Expression of the transgene was checked as green fluorescence inside the cells under a fluorescence microscope with FITC filter [lacuna] 24, 48 and 72 hours and then each subsequent week.

As soon as 24 hours after the transduction a slight fluorescence was visible and became distinctly stronger in subsequent days. The human IPE cells were 100% transduced with 100 MOI, and the rat cells were 80% transduced with 20 MOI and 100% transduced with 50 and 100 MOI. Expression was detectable in vitro for a period of up to 8 weeks or longer.

In a further experiment, the adenoviral vector of large DNA capacity AdhCMV.PEDF was constructed. This vector expresses the human PEDF cDNA under the control of the human CMV promoter. The PEDF protein is additionally tagged by a poly-histidine epitope expressed as fusion protein with the PEDF. This vector was produced by a standard method (Schiedner G, Morral N, Parks RJ, Wu Y, Koopmans SC, Langston C, Graham FL, Beaudet AL, Kochanek S (1998) Genomic DNA transfer with a high capacity adenovirus vector results in improved in vivo gene expression and decreased toxicity. Nature Genetics 18: 180–183) in Cre-recombinase-expressing 293 cells and purified by CsCl density gradient centrifugation.

Cytokeratin-positive human IPE cells from the $2^{nd}$ passage were transduced with the HC-Ad.CMV.PEDF vector. For this purpose, 80% confluent cell cultures in F12 complete medium were incubated with the appropriately diluted virus stock solution at 37° C. for 24 hours. The medium was changed next morning. Expression of the transgene and secretion of the PEDF into the culture supernatant were checked in an ELISA using specific anti-polyhistidine antibodies after 72 hours. The culture supernatants contained 150 ng PEDF/ml. This corresponds to a production of 60 pg of PEDF per 1000 cells in 72 hours. It was possible to detect in another ELISA using another antibody which specifically recognizes the human PEDF protein that human IPE cells do not, in contrast to human RPE cells, spontaneously produce PEDF.

IPE Sheet Transfection

It was possible to transfect not only single cells but also cell sheets. IPE cell sheets could be transfected after enzymatic removal of the basal membranes. The cell sheets with intact basal membrane could not be transfected, as was demonstrated by PCR.

For transfection of cell sheets, pig eyes were brought to the laboratory, and processed further, from the slaughterhouse immediately after the animals were slaughtered. The anterior segment was removed by a circular cut about 2 mm behind the limbus. The iris was then removed by a blunt dissection from the posterior direction and incubated in 1 ml Accutase at 37° C. for 15 min. The IPE is then detached from the stroma of the iris using a glass pipette bent in a flame. Estimation of the area of the individual IPE cell sheets obtained resulted in between 40,000 and 70,000 IPE cells per cell sheet.

The IPE sheets were incubated with 200 MOI of the EGFP-expressing adenoviral vector HC-AdFK7 for 24 h. The medium was changed after 24 hours. The IPE sheets were cultivated in F12 complete medium for 6 days and investigated for EGFP fluorescence, but it was not possible to demonstrate this with certainty because of the morphology of the cells with very densely concentrated melanin granules. DNA was then obtained from the cells using the QIAmp DNA mini kit (Qiagen). The manufacturer's instructions were followed. The transgene was detected by PCR using the primers prod1, which binds in the region of the CMV promoter, and prod2, which binds in the region of the EGFP sequence, to the DNA of HC-AdFK7. With successfully transduced cells, prod1 and prod2 produced a PCR product with a length of about 700 base pairs. A plasmid pFK7 with the same insert as is to be found in HCAdFK7 served as positive control.

6. Subretinal Transplantation of Genetically Modified Cells

8 Wistar rats received subretinal transplantation, in 8 eyes, of IPE cells, transduced with HC-AdFK7 vector, from Long Evans rats (albinotic) by the same method as described for untransfected IPE cells.

Four eyes into which IPE cells had been transplanted were enucleated after 2 months, embedded in tissue freezing medium (Jung, Heidelberg, Germany) and frozen at −80C. Cryostat sections (7 μm) were, after thawing, embedded in Kaiser's glycerol gelantin (Merck, Darmstadt, Germany) and examined under a Zeiss Axiophot light microscope with an excitation wavelength of 400–400 nm and an emission wavelength of 470 nm. The subretinally transplanted IPE cells showed distinct expression of green fluorescent proteins.

For evaluation using the scanning laser ophthalmoscope (SL), the other 4 transfected rats were examined 14 days and 4 months after the transfection. The animals were anesthetized with Ketanest and evaluated using the scanning laser ophthalmoscope (Rodenstock, Munich). This entailed scanning of the retina of the rats with mydriasis in fluo mode with the infrared laser (780 nm), the argon green laser (514 nm) and argon blue laser (488 nm). In this mode, the instrument uses a fluorescein cutoff filter suitable for observing the EGFP fluorescence. The images were recorded by S-VHS video. The analog video images were copied digitally onto DV, and bitmaps were produced from representative sections and evaluated for area and intensity using the software Optimas 6.1.

During the observation period of 4 months, the intensity of fluorescence caused by the transfected IPE cells, and the extent of the transplanted areas in the fundus remained constant in all 4 eyes, i.e. expression of the transfected genes remained unchanged at the protein level.

7. Subretinal Injection of Free Vector for Genetic Modification of RPE Cells of the Host (in vivo Gene Therapy)

For subretinal injection of free vector in vivo, various concentrations of an HC adenovirus "HC-AdFK7" which harbors the EGFP (enhanced green fluorescent protein) gene under the control of a CMV (cytomegalovirus) promoter as transgene were injected subretinally into Wistar rats. Expression of the transgene were evaluated using the scanning laser ophthalmoscope (Rodenstock, Munich). This entailed scanning of the retina of the rats with mydriasis in fluo mode with an infrared laser (780 nm), the argon green laser (514 nm) and argon blue laser (488 nm). In this mode, the instrument uses a fluorescein cutoff filter suitable for observing the EGFP fluorescence. The images were recorded by S-VHS video. The analog video images were copied digitally onto DV, and bitmaps were produced from representative sections and evaluated for area and intensity using the software Optimas 6.1.

During the observation period of 6 months, the intensity of the fluorescence caused by the transfected IPE cells, and the extent of the transplanted areas in the fundus remained constant in all 4 eyes, i.e. expression of the transfected genes remained unchanged at the protein level. After 6 months, the animals were sacrificed, and the eyes were fixed in 3% glutaraldehyde. The anterior segments of the eyes were removed and the remaining posterior optic cups were divided into four. After the retinas had been removed, the sclera, choroid with pigment epithelium were examined under a fluorescence microscope (Axiovert Zeiss, Oberkochen, Germany) using a 450–490 nm excitation filter and a 520 nm emission filter (AF Analysentechnik, Tübingen, Germany). This revealed the typically hexagonal shape of transduced and EGFP-positive pigment epithelial cells.

8. Transplantation of Genetically Modified Cells into the CNS

For transplantation of genetically modified cells into the CNS, IPE cells (60000) which had been transduced with HC-AdFK7 vector and expressed EGFP from Long Evans rats were stereotactically injected as described above into the striatum of each of 4 Wistar rats.

After 8 weeks, the animals were sacrificed by cervical dislocation under $CO_2$ anesthesia. The brains were dissected out. Pigmented areas with transplanted cells were excised from the striatum and frozen in tissue freezing medium (Jung, Heidelber, Germany). The fluorescence caused by the expression of EGFP by the IPE cells was detectable in frozen sections 8 weeks after transplantation in pigmented cells.

9. Prevention of Choroidal Neovascularization [lacuna] Genetically Modified and PEDF-Expressing IPE Cells in vivo IPE cells were cotransfected with the adenoviral vector of large DNA capacity HC-AdFK7, which harbors the EGFP (enhanced green fluorescent protein) gene under the control of a CMV (cytomegalovirus) promoter as reporter gene, and simultaneously with the PEDF-expressing adenoviral vector of large DNA capacity HC-AdCMV.PEDF in vitro and, after 6 days, transplanted into the subretinal space of Long Evans rats (60,000 cells/eye) ($1^{st}$ experimental group). The PEDF expression cassette in the adenoviral vector of large DNA capacity contained a poly-HIS epitope for detecting the protein using an anti-HIS antibody in addition to the PEDF-encoding sequence. One week after injection, the rats were anesthetized, the pupils were dilated and the rats received 3–4 laser burns around the optic nerve with a blue-green argon laser (Coherent, Inc., Santa Clara, Calif., USA). The energy of the laser was 90 mW for 100 ms, and the diameter of the beam was 100 μm. A second group of rats received only laser burns without genetic modification by cell transplantation or free vectors. After 16 days, the rats were anesthetized and received 0.5 ml Liquemin i.p. (Roche, Grenzach-Wyhlen, Germany). The ascending aorta was canulated and, after the right atrium was opened, the blood was washed out with 50 ml of Ringer lactate solution (Stereofundin, Braun, Melsungen, Germany). This was followed by perfusion with 20 ml of Ringer solution with 5 mg/ml FITC dextran (Sigma Deisenhofen, Germany). The eyes were enucleated, pierced with a scalpel at the level of the limbus and fixed in 4% paraformaldehyde overnight. The next day, the anterior segment of the eyes was removed up to a short distance behind the ora serrata by a circular incision. The remaining optic cup was divided into quadrants by 4 radial incisions, and the retinas were removed. Quadrants consisting of pigment epithelium, choroid and sclera containing laser scars were incubated in tris buffer (TBS) for 4×10 min and then in 0.5 M $NH_4CL$ (Sigma, Deisenhofen, Germany) and 0.25% Triton (Serva, Heidelberg, Germany) for 10 min. After two further washes, the specimens were incubated with 5% BSA (Albumin, Bovine Fraction Sigma, Deisenhofen, Germany). Some of the specimens were incubated with antibodies against histidine (anti-His antibody, Qiagen, Hilden, Germany) in order to detect the histidine residues in the PEDF. The primary antibodies were visualized using anti-mouse IgG coupled to the fluorescent dye Cy3 (Rockland, Gilbertsville, Pa., USA).

Other specimens were treated with rat anti-mouse CD 31 (PECAM-1, Pharmingen, San Jose, Calif., USA) in order to visualize the endothelial cells. This was followed by a $2^{nd}$ incubation with anti-rat IgG-biotin (Amersham, Pharmacia Biotech Europe GmbH, Freiburg, Germany) with subsequent localization of the biotin by Fluorolink Cy3 (Amersham Life Sciences, Braunschweig, Germany). Some choroid specimens underwent double labeling of PEDF and endothelial cells. In these cases, PEDF expression was visualized with Cy3 as described, and the PECAM-biotin complex was visualized with streptavidin-Alexa Fluor 350 (MoBiTec, Gottingen, Germany).

The flatmount specimens were evaluated under the fluorescence microscope (Axiophot, Zeiss, Oberkochem, Germany).

In group 1 there was no observable escape of FITC-dextran nor an increased occurrence of CD 31-positive cells in 16 of 19 laser scars when PEDF-expressing IPE cells were present at a distance of 100–1000 μm from the scar. The expression of PEDF by the transplanted IPE cells was demonstrated with anti-His antibodies.

In the control group 2 (only laser burn), neovascularization was present in 9 of 12 laser scars. This was evident from the escape of dextran-FITC in and around the scar region and from the presence of flattened CD 31-positive endothelial cells in and around the scar region.

Neovascularization was thus detected in the same eye with a functional (dextran leakage) and an immunological method (direct detection of the newly produced endothelial cells with antibodies). These flatmount specimens allow the entire choroid to be assessed. These results show that neovascularization is inhibited by transplantation of IPE cells which express PEDF of an adenoviral vector of large DNA capacity.

10. Endogenous and HC-Ad Vector Mediated Production of PEDF in IPE and RPE Cells Endogenous PEDF production in nontransduced RPE and IPE cells was determined. RPE cells secreted 96+9.5 ng/ml PEDF within 72 h (n=4), while endogenous PEDF was not detected in supernatants from IPE cells (detection limit 1.56 ng/ml). Thus, IPE cells, in contrast to RPE cells, were found to lack the expression of PEDF, a protein that is believed to play a key role in the homeostasis of the retina.

Figure 2:
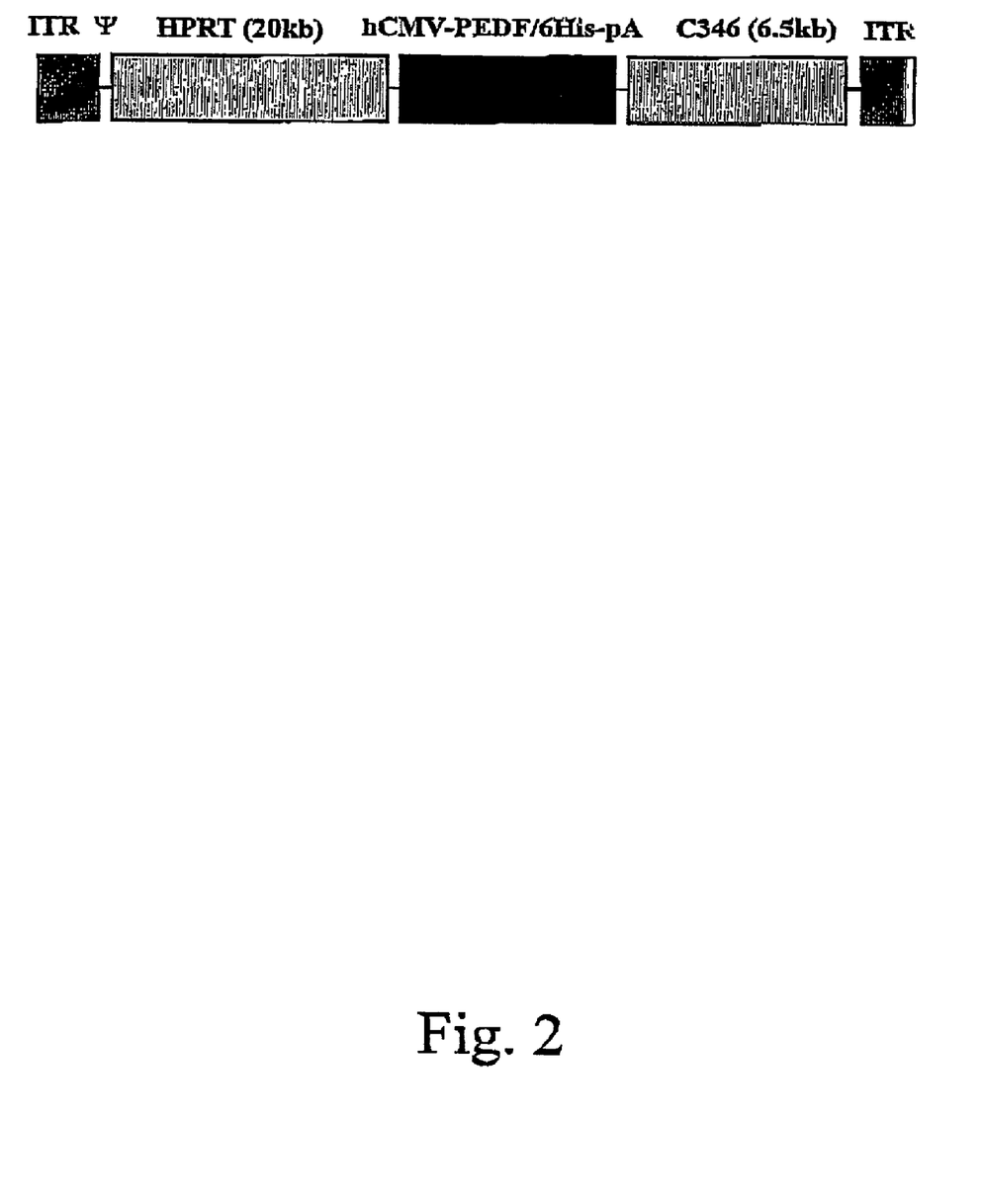
FIG. 2 Genomic structure of HC-Ad.PEDF.

The vector HC-Ad.PEDF was constructed to express the human PEDF carrying a C-terminal 6-His tag (FIG. 2). IPE (Hu, D. N., Ritch, R., McCormick, S. A. & Pelton-Henrion, K. (1992) Invest Ophthalmol Vis Sci 33, 2443–2453) and RPE (Chang, C. W., Defoe, D. M. & Caldwell, R. B. (1997) Invest Ophthalmol. Vis. Sci. 38, 188–195) cell cultures were prepared from Long Evans rats. Early passage cultures of choroidal endothelial cells (hCEC) (positive for v.Willebrand factor) were obtained from donor eyes (Hoffmann, S., Spee, C., Murata, T., Cui, J. Z., Ryan, S. J. & Hinton, D. R. (1998) Graefes Arch Clin Exp Ophthalmol 236, 779–784). $1 \times 10^6$ IPE cells were transduced with 50 MOI of HC-Ad.PEDF for 24 h. 48 h and 72 h after medium change supernatants were collected. PEDF released into the medium was detected by ELISA with mouse penta-his (5 g/ml; Qiagen) and anti-PEDF antibodies (1 μg/ml, Chemicon). Endogenous PEDF production was determined from non-transduced IPE and RPE cells. Standard curves were generated from known amounts of recombinant PEDF.

Following transduction of IPE cells with HC-Ad.PEDF vector IPE cells ($1 \times 10^6$ cells/dish, n=4) secreted 250+38 ng/ml PEDF into the supernatant within 72 h. IPE cells secreted functionally active PEDF at high levels following HC-Ad mediated gene transfer.

To examine effects of IPE-produced PEDF on hCEC function IPE cells were transduced with 50 MOI of HC-Ad.PEDF or 50 MOI of HC-Ad.FK7. Undiluted, 1:10 or 1:100 diluted supernatants (conditioned media =CM) collected 72 hours after medium change were added to hCECs.

To analyze proliferation, $1 \times 10^3$ hCECs/well seeded in 96-well plates were exposed to CM with or without 50 ng/ml VEGF (Sigma) and with or without 1 μg/ml anti-PEDF antibody. Five days later, cellular proliferation was determined using the WST-1 proliferation assay (Roche). Non-diluted and 1:10 diluted CM from HC-Ad.PEDF transduced IPE cells reduced VEGF-stimulated proliferation of hCECs without having any effect on unstimulated proliferation. Anti-PEDF antibody (1 μg/ml), present in the CM, abolished the inhibitory effect. CM from HC-Ad.FK7 transduced and nontransduced IPE cells did not influence both stimulated and nonstimulated proliferation of the cells.

To analyze migration, $5 \times 10^3$ hCECs/insert were incubate in modified Boyden chambers (Tang, S., Gao, Y. & Ware, J. A. (1999) J. Cell Biol. 147, 1073–1084) (FluoroBlock inserts, Becton Dickinson) in CM with or without VEGF (50 ng/ml) for 8 h at 37° C. Migrated cells were visualized by the nuclear fluorescence dye (DAPI, Alexis) and counted in three random fields/membrane. CM from HC-Ad.PEDF transduced IPE cells reduced the migration of hCECs towards angiogenic VEGF from 47.5+5.9 to 14.3+5.7 cells/membrane (P<0.001).Exposure to CM from HC-Ad.FK7 transduced and nontransduced IPE cells did not influence hCECs migration.

To determine the formation of capillary-like tubes in response to PEDF, $1 \times 10^4$ hCECs/well were seeded in 96-well plates coated with VEGF-containing ECM gel (Chemicon) for 24 h in CM. CM from HC-Ad.PEDF infected IPE cells suppressed neovascular tube formation while supernatants from HC-Ad.FK7 transduced and non-transduced IPE cells had no effect.

11. Long-Term EGFP Expression Following Subrethial Transplantation of HC-Ad.FK7 Transduced IPE Cells IPE cells were transduced with 50 MOI of HC-Ad.FK7 or were co-transduced with 50 MOI of HC-Ad.PEDF and HC-Ad.FK7. Before transplantation the medium was changed, the cells were washed twice with PBS, and suspensions of $5 \times 10^4$ cells/μl were transplanted (1 μl/eye). Transplantation was performed as aforementioned.

EGFP fluorescence in Wistar rats was monitored 7 days, 1, 2, 3 and 4 months after subretinal injection of HC-Ad.FK7 transduced IPE cells by Scanning Laser Ophthalmoscopy (SLO, Rodenstock, Germany), and on RPE-choroidal flat-mounts (McMenamin, P. G. (2000) Invest Ophthalmol Vis Sci 41, 3043–3048) by fluorescence microscopy (Axioplan, Zeiss, Germany). Four months after injection, the areas of HC-Ad.FK7 transduced IPE transplants were subjected to electron microscopy. PEDF expression in IPE transplants was visualized in 4% paraformaldehyde fixed RPE-choroidal flatmounts and in paraffin sections using penta-his antibody (5 μg/ml) and Cy3 (Amersham) or peroxidase (Amersham) conjugated secondary antibodies.

Seven days after transplantation of HC-Ad.FK7 transduced IPE cells areas of patchy and/or continuous fluorescence was observed by SLO at the site of injection. Three months later, areas of bright EGFP fluorescence were still present in the same eyes with comparable extension and intensity as at 1 and 2 month. Four months after surgery, EGFP expressing IPE cells were found integrated into the host RPE layer as determined in RPE-choroidal flatmounts. By electron microscopy, pigmented IPE cells formed a second layer on the RPE of the Wistar hosts. The rod outer segments facing the transplants appeared morphologically intact. Thus, genetically modified IPE cells formed a monolayer following transplantation and stably expressed an EGFP reporter for at least 4 months without adverse effects.

12. Effects of HC-Ad Vector Mediated PEDF Expression from Transplanted IPE Cells in a Model of Oxygen-Induced Retinal Neovascularization A previously described model of ischemia-induced retinopathy (Smith, L. E., Wesolowski, E., McLellan, A., Kostyk, S. K., D'Amato, R., Sullivan, R. & D'Amore, P. A. (194) Invest Ophthalmol Vis Sci 35, 101–111) was set up by using Wistar rats. Animals in the normoxia group were maintained in room air throughout the experiment. Rats in the hyperoxia groups were exposed to 75% oxygen from postnatal day 7 (P7) to P12, then removed to room air and immediately transplanted subretinaly with 1) nontransduced IPE cells; 2) IPE cells transduced with HC-Ad.FK7; 3) IPE cells co-transduced with HC-Ad.PEDF and HC-Ad.FK7. At P 22, the animals were anesthetized and perfused with 50 mg/ml fluorescein isothiocyanate-dextran (Sigma) as described (Smith et al., supra). The neovascularization was investigated on retinal-RPE-choroidal flatmounts using a fluorescence microscope. To quantify neovascularization the length of newly formed tortuous blood vessels with diameters larger than 25 $\mu$m on the inner surface of peripheral retina was determined by computer assisted morphometry (Openlab software; ImproVision, Inc., Lexington, USA). For quantification the angiographic images were digitalized and subsequently processed. Vessels were classified according to their diameters. Measurements of the vessel length were taken in areas of 800 000 $\mu m^2$ per eye located up to 200 $\mu$m from the transplanted IPE cells or in corresponding peripheral regions of hyperoxia controls. Additionally to the vessel length, a second independent quantification of neovascularization was performed by evaluation of the total vascularized area on the same peripheral regions. The fluorescence images were evaluated by setting of threshold level of fluorescence, above which the superficial retinal vessels but not the vessels of retinal deep plexus were captured. Vascularized areas were normalized to the total evaluated peripheral retinal area. Furthermore, to confirm epiretinal localization of the superficial pathological vessels 10 $\mu$m serial frozen sections were prepared cut through half of the eye. Immunofluorescence microscopy was performed as aforementioned.

At P22 on flatmounts from hyperoxia-exposed nontransplanted animals, large peripheral areas with dilated radial vessels, microaneurysms and hemorrhages, typical for retinal neovascularization were observed. These were not present in retinas from normoxia controls. Typical signs of peripheral retinal neovascularization characterized by vascular tufts, dilated vessels with abnormal tortuous courses on the inner surface of the peripheral retina were evident. The epiretinal position of the newly formed pathological vessels was evident in cryosections. IPE cell transplants were localized in the peripheral areas of flatmounts between the RPE layer and the neuronal retina. IPE cells were identified by EGFP expression and their preserved hexagonal shape. HC-Ad.PEDF transduced IPE implants prevented the formation of pathological tortuous vessels in the areas of transplantation. Immunofluorescence microscopy documented the expression of PEDF from genetically modified IPE transplants. The overall effects of the IPE transplants on the formation of pathological vessels are summarized in. IPE transplants were located in the periphery where typical pathological vessels are usually formed after exposure to hyperoxia in this model (Smith et al., supra). To quantify the neovascularization the length of dilated tortuous vessels on the inner surface of the retina with diameters larger than 25 $\mu$m were measured on retinal areas of 800 000 $\mu m^2$ per eye. Evaluated areas were localized up to 200 $\mu$m from IPE transplants or in corresponding peripheral regions of hyperoxia controls. Similar as in normoxia controls, in the vicinity of PEDF expressing IPE cells pathological epiretinal vessels were absent. Nontransduced IPE cell transplants did not influence pathological vascularization compared to hyperoxia controls. Additionally to the vessel length, the sizes of vascularized areas (superficial vessels) were determined as an independent parameter of neovascularization. Close to PEDF expressing IPE cells the sizes of vascularized areas were reduced to 0.0153±0.0081 $\mu m^2$ blood vessels per $\mu m^2$ tissue in comparison to 0.0546±0.014 $\mu m^2$ blood vessels/$\mu m^2$ tissue in retinal regions with transplanted non-transduced IPE cells. Thus, subretinal transplantation of PEDF-expressing IPE cells prevented neoangiogenesis in a model of oxygen-induced neovascularization.

13. Effects of HC-Ad Vector Mediated PEDF Expression from Transplanted IPE Cells in a Model of Laser Induced Choroidal Neovascularization (CNV)

IPE cells were subretinally transplantated into 4–5 months old Long Evans rats. Six days later laser photocoagulation (100 $\mu$m spot size, 0.1 sec duration, 150 mW) was performed using blue-green setting of a coherent Novus 2000 argon-laser (Coherent Inc., USA) close to the transplanted IPE cells (3 burns/eye). Ten days after transplantation choroidal neovascularization was evaluated on RPE-choroidal flatmounts by labeling endothelial cells with a rat anti-mouse CD31 (PECAM-1) monoclonal antibody (1 $\mu$g/ml; Becton Dickinson). The sizes of the areas occupied with endothelial cells were determined by computer assisted morphometry. The burns were classified: type I—100% occupied; type II—completely free from endothelial cells; type III—both occupied and endothelial cell free areas present.

Laser scars were identified on bright field images by pigment clumping. Fluorescence micrography of a laser burn from nontransplanted laser controls after labeling of the endothelial cells with the anti-PECAM-1 antibody revealed that the burn (type I) is completely (100%) occupied with newly formed endothelial cells. IPE transplants were localized surrounding the laser burnsig. The existence of EGFP expressing IPE cells (co-transduced with HC.AdFK7 and HC-Ad.PEDF) close to 3 laser burns could be prooven. These IPE transplants strongly expressed PEDF as detected by staining with the penta-his antibody. The presence of PEDF expressing IPE transplants close to the site of damage prevented formation of new vessels within the laser burns. These laser burns were classified as type II burns, completely free from endothelial cells. Furthermore, PEDF expressing IPE cells (about 100) surrounding the burn reduced the area of neovascularisation compared to non-transplanted laser controls. In this case, newly formed endothelial cells occupied 67% (47,400 $\mu m^2$) of the whole area within the burn (70,500 $\mu m^2$). Endothelial cells remained at the margin of the scar and did not proliferate or migrate into the center of the burn. The areas free of endothelial cells within the burn were localized close to transplanted IPE cells. Table 2 summarizes the classification of laser burns based on the size of CNV areas in the different experimental groups. Both EGFP expressing IPE and nontransduced IPE transplants did not influence laser induced CNV formation. Thus, subretinal transplantation of PEDF-expressing IPE cells prevented neoangiogenesis in a model of laser-induced neobascularization.

TABLE 2

Classification of laser burns based on the sizes of CNV areas.

| Experimental Groups Evaluated | Laser controls | | Close to PEDF expressig IPE cells | | Close to EGFP expressig IPE cells | | Close to Non transduced IPE cells | |
|---|---|---|---|---|---|---|---|---|
| laser burns | n = 31 | (%) | n = 18 | (%) | n = 6 | (%) | n = 5 | (%) |
| I. Burns Completely vascularized | 28 | 90.3 | 0 | 0 | 6 | 100 | 5 | 100 |
| II. Burns Completely free from new vessels | 0 | 0 | 6 | 33.3 | 0 | 0 | 0 | 0 |
| III. Burns with vascularized and non-vascularized areas | 3 | 9.7 | 12 | 66.6 | 0 | 0 | 0 | 0 |

14. Effects of HC-Ad Vector Mediated PEDF Expression from Transplanted IPE Cells on Photoreceptor Rescue in a Model of Retinal Degeneration Two months after transplantation of IPE cells into 20 days old RCS rats (Schraermeyer, U., Kociok, N. & Heimarm, K. (1999) Invest Ophthalmol Vis Sci 40, 1545–1556) the animals were sacrificed and 5 µm thick paraffin sections were prepared cut through half of the eye. After H&E staining, rescue effects were quantitated by determining the number of rows and size of areas with preserved photoreceptor nuclei in all sections. Rhodopsin expression was detected with rhodopsin antibody (5 µg/ml, Leinco Technol.) and peroxidase-labeled secondary antibody. The sizes of areas with preserved rhodopsin-containing outer segments were determined using computer assisted morphometry.

Only few photoreceptor nuclei were present close to IPE cells which had been transduced with the EGFP-expressing HC-Ad.FK7 vector alone. However, several rows of photoreceptor nuclei were preserved adjacent to the HC-Ad.PEDF vector transduced IPE transplants. In these areas by immunofluorescence microscopy PEDF was found to be expressed from HC-Ad.PEDF transduced IPE transplants. In these sections the number of photoreceptor rows was significantly higher (4.4+0.68, $P<0.05$) compared to HC-Ad.FK7 transduced (2.18+0.29) and nontransduced IPE transplants (2.2+0.55). In addition, in sections with PEDF expressing cells (n=9), the areas with preserved photoreceptor nuclei (more than 5 rows) had a length of 2.6+1.0 mm. Preserved rhodopsin was present in rod outer segments of the survived photoreceptors in the vicinity of PEDF expressing cells. In the same sections a rhodopsin positive area of 53 947+24 656 µm$^2$ (n=5) measured. In sections with HC-Ad.FK7 transduced or in nontransduced IPE transplants rhodopsin staining was not detectable. Thus, subretinal transplantation of PEDF-expressing IPE cells prevented photoreceptor degeneration in a model of retinal degeneration.

15. Effects of HC-Ad Vector Mediated PEDF Expression in RPE Cells in a Model of Laser Induced Choroidal Neovascularization $5\times10^6$ infectious particles of HC-Ad.PEDF and HC-Ad.FK7 in a final volume of 0.5 µl were injected into the subretinal space of 4–5 months old Long Evans rats. Thereafter, laser photocoagulation (100 µm spot size, 0.1 sec duration, 150 mW) was performed using blue-green setting of a coherent Novus 2000 argonlaser (Coherent Inc., USA) close to the site of injection (3 bums/eye). Ten days after transplantation choroidal neovascularization was evaluated on RPE-choroidal flatmounts by labeling endothelial cells with a rat anti-mouse CD31 (PECAM-1) monoclonal antibody (1 µg/ml; Becton Dickinson). The sizes of the areas occupied with endothelial cells were determined by computer assisted morphometry. The bums were classified as indicated in table 2 (type I to III).

In such lesions areas free of endothelial cells were always present. Expression of PEDF by the transplants was analyzed using specific antibodies. In the controls (only laser-burns) only 10% of the laser-bums lacked neovascularization, whereas in the other 90% the areas of these scars were completely filled with endothelial cells as detected by staining using a CD 31 antibody. All (100%) scars were completely free of newly formed endothelial cells if PEDF expressing RPE cells were surrounding the lesions at a distance of 100 µm or closer. In this model choroidal neovascularization was detected by an immunological method in the same laser lesion. Thus, injection of the PEDF-expressing HC-Ad vector into the subretinal space prevented neoangiogenesis in a model of laser-induced neovascularization.

16. Effects of HC-Ad Vector Mediated PEDF Expression in RPE Cells in a Model of Oxygen-Induced Retinal Neovascularization In these experiments Wistar rats were used. Animals in the normoxia group were maintained in room air throughout the experiment. Rats in the hyperoxia groups were exposed to 75% oxygen from postnatal day 7 (P7) to P12, then removed to room air and immediately injected subretinaly with $5\times10^6$ infectious particles of HC-Ad.PEDF and HC-Ad.FK7 in a final volume of 0.5 µl. At P 22, the animals were anesthetized and perfused with 50 mg/ml fluorescein isothiocyanate-dextran (Sigma, Deisenhofen, Germany). The neovascularization was investigated on retinal-RPE-choroidal flatmounts using a fluorescence microscope. To quantify neovascularization the length of newly formed tortuous blood vessels with diameters larger than 25 µm on the inner surface of peripheral retina was determined by computer assisted morphometry (Openlab software; ImproVision, Inc., Lexington, USA). Measurements of the vessel length were taken in areas of 800 000 μm² per eye located up to 200 μm from the transfected RPE cells or in corresponding peripheral regions of hyperoxia controls. Furthermore, to confirm epiretinal localization of the superficial pathological vessels 10 μm serial frozen sections were prepared cut through half of the eye.

At P22, on flatmounts from hyperoxia-exposed nontransplanted animals, large peripheral areas with dilated radial vessels, microaneurysms and hemorrhages, typical for retinal neovascularization were observed. These were not present in retinas from normoxia controls. Typical signs of peripheral retinal neovascularization characterized by vascular tufts, dilated vessels with abnormal tortuous courses on the inner surface of the peripheral retina were evident. The epiretinal position of the newly formed pathological vessels was evident in cryosections. Transfected RPE cells were localized in the peripheral areas of flatmounts. Transfected RPE cells were identified by EGFP expression. HC-Ad.PEDF transduced RPE cells prevented the formation of pathological tortuous vessels in the areas of transfection. Immunofluorescence microscopy documented the expression of PEDF from genetically modified RPE cells. Transduced RPE cells were located in the periphery where typical pathological vessels are usually formed after exposure to hyperoxia in this model. At a distance of 200 μm or larger from transfected RPE cells dilated tortuous newly formed vessels on the inner surface of the retina with diameters larger than 25 μm were regularly present. Similar as in normoxia controls, in the vicinity of PEDF expressing RPE cells pathological epiretinal vessels were absent. Thus, oxygen induced retinal neovascularization was locally inhibited by HC-Ad vector mediated expression of PEDF in RPE cells.

17. Statistics

All data are means±SEM from at least three experiments with 3 to 6 determinations. For multiple comparisons one-way analysis of variance (ANOVA) was used with subsequent post hoc analysis (Duncan test).

The invention claimed is:

1. A method for producing a pigment epithelial cell of the eye comprising an adenoviral vector, the method comprising introducing an adenoviral vector to the pigment epithelial cell of the eye and cultivating the cell in serum-free medium and in the presence of a feeder layer, the adenoviral vector comprising at least one expressed nucleic acid operatively linked to a promoter, said vector comprising neither adenoviral nor *E. coli* coding DNA sequences.

2. The method as claimed in claim 1, wherein the pigment epithelial cell of the eye is a retinal pigment epithelial cell.

3. The method as claimed in claim 1, wherein the nucleic acid expresses a protein selected from the group consisting of a neurotrophic factor, an antiangiogenic factor, an antioxidative factor, a lysosomal factor, and a vasodilating factor.

4. The method as claimed in claim 3, wherein the protein is selected from the group consisting of GDNF, PEDF, NGF, BDNF, CNTF, bFGF, neurotrophin 3,4-5, a soluble VEGF receptor-1 (sflt-1), a dominant-negative VEGF receptor-2 (KDR), PEDF, superoxide dismutase, catalase, peroxidase, alpha-mannosidase, beta-galactosidase, N-acetyl-beta-glucosaminidase, N-acetyl-beta-galactosaminidase, lipase, and NO synthase.

5. The method as claimed in claim 1, wherein the promoter is selected from the group consisting of a constitutively active promoter, a regulatable promoter, and a tissue-specific promoter.

6. The method as claimed in claim 1, wherein the cell expresses at least one protein encoded by said expressed nucleic acid.

7. The method as claimed in claim 1, wherein the cell expresses at least one RNA from said expressed nucleic acid.

* * * * *